United States Patent [19]

Reed

[11] Patent Number: 4,855,045
[45] Date of Patent: Aug. 8, 1989

[54] METHOD AND APPARATUS FOR THE SEPARATION OF ORGANIC SUBSTANCES FROM A SUSPENSION OR SOLUTION

[76] Inventor: Thomas A. Reed, Otto-Hahn-Platz 7, D-6900 Heidelberg-Emmertsgrund, Fed. Rep. of Germany

[21] Appl. No.: 890,807
[22] PCT Filed: Jan. 13, 1983
[86] PCT No.: PCT/DE83/00003
§ 371 Date: Sep. 14, 1983
§ 102(e) Date: Sep. 14, 1983
[87] PCT Pub. No.: WO83/02404
PCT Pub. Date: Jul. 21, 1983

Related U.S. Application Data

[63] Continuation of Ser. No. 537,361, Sep. 14, 1983, abandoned.

[30] Foreign Application Priority Data

Jan. 14, 1982 [DE] Fed. Rep. of Germany ....... 3200988

[51] Int. Cl.⁴ .............................................. B03C 1/30
[52] U.S. Cl. .................................... 210/223; 210/222; 210/502.1; 435/178; 435/180
[58] Field of Search ............... 435/173, 176, 177, 178, 435/179, 180, 2; 210/216, 219, 222, 223, 695, 502.1; 209/223.1, 232

[56] References Cited

U.S. PATENT DOCUMENTS

| 3,360,672 | 8/1969 | Imris .......................................... 209/1 |
| 3,843,450 | 10/1974 | Satholm ............................... 435/287 |
| 3,871,961 | 3/1975 | Gianessi .............................. 435/287 |
| 4,152,210 | 5/1979 | Robinson et al. .................... 195/63 |
| 4,219,411 | 8/1980 | Yen et al. ........................... 209/223.1 |
| 4,261,828 | 8/1981 | Brunner et al. ..................... 210/287 |
| 4,495,074 | 1/1985 | Hagiwara et al. ................... 210/695 |
| 4,596,283 | 6/1986 | Ciprios et al. ...................... 210/695 |
| 4,780,113 | 10/1988 | Koslow ............................... 210/695 |

FOREIGN PATENT DOCUMENTS

| 1017102 | 10/1957 | Fed. Rep. of Germany . |
| 0179482 | 10/1983 | Japan ................................... 435/287 |
| 8200660 | 3/1982 | PCT Int'l Appl. ................. 435/176 |
| 8100575 | 3/1981 | Sweden ............................... 435/172 |
| 819367 | 9/1959 | United Kingdom . |
| 1386303 | 3/1975 | United Kingdom . |
| 2034719 | 6/1980 | United Kingdom ................ 435/176 |

OTHER PUBLICATIONS

Paul et al., IEE Trans on Magnet.–17, No. 6, Nov. 1981, pp. 2822-2827.
Guedson et al., *Chem Abst.*, vol. 89, No. 74020r, 1978, "Magnetically Responsive Polyacrylanide Agarose Beads for the Preparation of Immunoadsorbent".

*Primary Examiner*—W. Gary Jones
*Attorney, Agent, or Firm*—Toren, McGeady & Associates

[57] ABSTRACT

A method and apparatus for the separation of cells, organelles or proteins from a suspension or solution thereof, including:
(a) coating ferromagnetic beads with an adsorption layer comprising antibodies, haptenes or chemical substrate adapted for binding the cells, organelles or proteins to be separated;
(b) introducing said beads to a separation chamber having an entrance port and an exit port, the ratio of total volume of said beads to the chamber volume being of between 0.01 and 0.5, said chamber having magnetic field gradients in the regions of said entrance and exit ports to prevent the beads from leaving the chamber through the entrance or exit ports; and
(c) passing the suspension or solution containing said cells, organelles or proteins into the entrance port through the chamber and out of the exit port to effect adsorption of the cells, organelles or proteins on said adsorption layer of the beads.

14 Claims, 3 Drawing Sheets

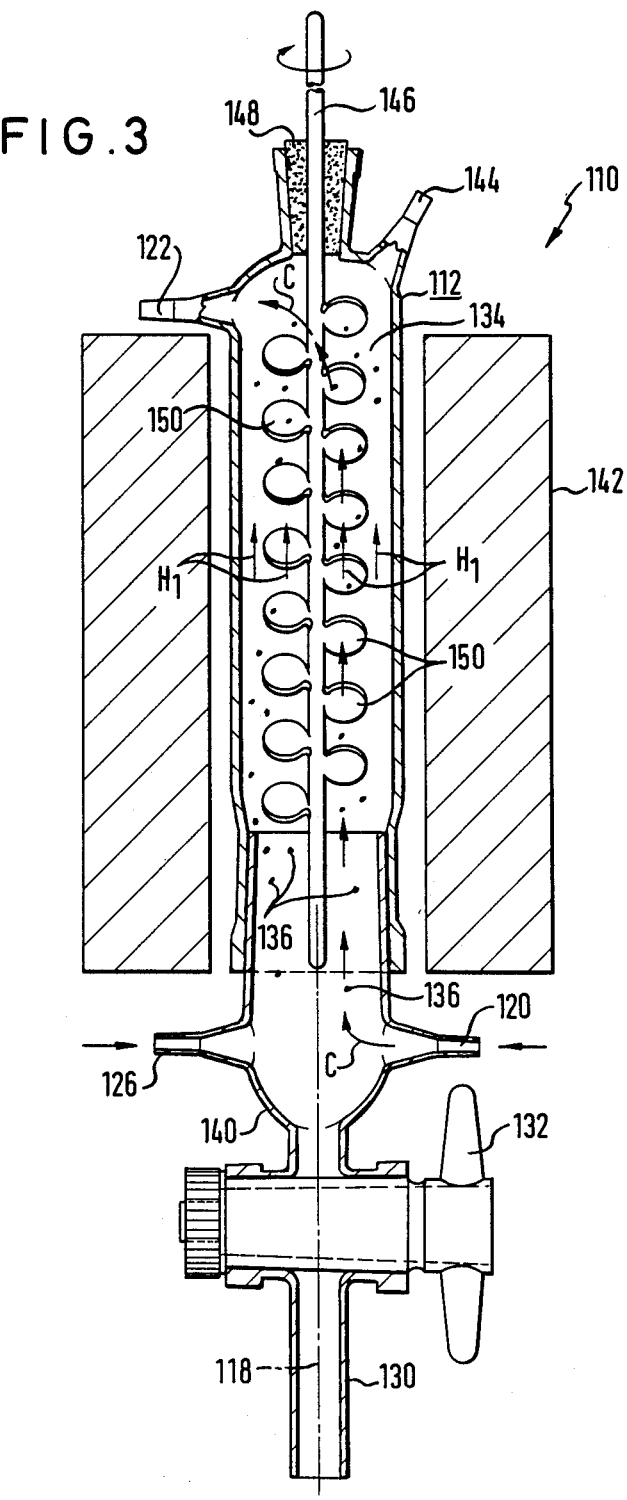

METHOD AND APPARATUS FOR THE SEPARATION OF ORGANIC SUBSTANCES FROM A SUSPENSION OR SOLUTION

This is a continuation of application Serial No. 537,361, filed Sept. 14, 1983, now abandoned.

The invention relates to a method for the separation of organic substances, more especially cells, organelles and proteins, from a suspension or solution flowing through a reaction space by attaching the organic substances to attachment bodies inside the reaction space in the form of pearls or the like, whose surfaces may be provided with an absorption layer which acts specifically on the respective organic substance.

For the separation of biological cells or organelles, it is known to use pearl-shaped attachment bodies, whose surfaces mainly bind specific cells or organelles. This can be achieved in that special antibodies, haptenes or chemical substrates are covalently attached to the surface of the attachment bodies which, in turn, exclusively or mainly bind special cells or organelles. Once the attachment of the cells or organelles has been effected, the substances not bound to the surface of the attachment bodies can be washed away; subsequently, the substances bound by the attachment bodies can be detached from the attachment bodies with the aid of appropriate methods.

In a known method of the kind mentioned at the beginning, the attachment bodies are contained in a dense package within a so-called separating column, through which the suspension containing the organic substances flows. This arrangement has the disadvantage that, on account of the attachment bodies being packed densely, the separating column offers a high degree of flow resistance so that the suspension flows through the separating column at a low flow velocity. This results in a correspondingly long sojourn time of at least half an hour and up to 2 or 3 hours. This long sojourn time is disadvantageous not only because it impairs the economy of the method but also because this increases the probability of undesirable substances being attached to the attachment bodies in a non-specific bond in such a way that they are not removed in the subsequent normal washing process step. The product finally separated from the absorption bodies therefore contains not only the desired special cells or organelles. Another disadvantage of the known method lies in the fact that cells or organelles and proteins, including the undesirable non-specific cells, organelles or proteins, may be enclosed in the small spaces between the attachment bodies which are in abutting contact with one another. On account of these disadvantages, the use of this method has been confined to preparatory quantities of organic substances to be separated. An enlargement of the plant for cell or organelle suspensions of more than 50 or 100 ml presented considerable difficulties.

It is therefore the object of the invention to reduce the throughput time in a process of the kind mentioned at the beginning without impairing the separating effectiveness.

This problem is solved in that the magnetic, preferably ferromagnetic attachment bodies are kept at a distance from one another in an open arrangement in the reaction space by magnetic field gradients in a ratio of the total volume of the attachment bodies to the reaction space volume of between 0.01 and 0.5, preferably between 0.02 to 0.4, and ideally between 0.03 and 0.2. Due to the distribution of the attachment bodies over the reaction space at a distance from one another in the stated volume ratios, there comes about a low flow resistance which allows a correspondingly high flow velocity of the suspension (i.e. the suspension containing the organic substances). It is virtually impossible for organic substances getting stuck between adjacent attachment bodies. The short throughput time allows the process to be extended beyond a laboratory operation. On account of the shortened sojourn time, the risk of undesirable cells or organelles being bound non-specifically to the attachment bodies is reduced. Due to the relatively high flow velocity, the non-specific cells or organelles are as a rule taken along by the flow so that the subsequent washing process step for removing these substances from the attachment bodies can be dispensed with or at least shortened. Surprisingly, it has turned out that, despite the reduced total surface of the attachment bodies, the separating effectiveness has remained substantially unchanged with a given reaction space volume. The reason for this is that the half-life period of typical specific bonding reactions between the special organic substances and the absorption layer of the attachment bodies ranges from 30 seconds to 20 minutes in dependence on the concentration of the attachment bodies and the concentration of the specific substrate on the attachment body surface. The bonding reaction is of the first order. The concentration of the specific cells or organelles may be at least $10^6$ per $cm^3$. If, according to the invention, the suspension containing the organic substances is therefore passed through the reaction volume in a relatively short time in accordance with the half-life period, then virtually all possible specific bonding reactions take place within this period. The absorption surface is consequently fully utilised, whereas in the known method there occur, on account of the sojourn time of the suspension in the reaction space exceeding by far the reaction half-life period, secondary reactions, particularly non-specific bonding reactions, which impair the separation result in spite of a considerable absorption surface (contamination of the end product by non-specific organic substances). It is also advantageous that the method according to the invention requires fewer attachment bodies which, in turn, improves the economy of the method. A loss of attachment bodies by their being taken along in the suspension stream is prevented in a simple manner by the magnetic field gradients which exert corresponding retention forces on the magnetic, preferably ferromagnetic attachment bodies.

In another known method for the separation of organic substances from a suspension, the attachment bodies are mixed with the suspension in a paste-like manner and are allowed to stand for some time for the specific attachment of the desired organic substances. The holding time is again at least half an hour to 3 hours. It is particularly disadvantgeous in this method that there has to be available a quantity of attachment bodies that corresponds to the total volume of the starting suspension, whereas in the method mentioned at the beginning the total volume of the starting suspension may be a multiple of the reaction space volume.

In a first constructional form (static arrangement) of the invention, the attachment bodies are held by a ferromagnetic carrier, which passes through the reaction space, on the surface thereof on account of magnetic field gradients in the zone of the surface of the carrier which is arranged in a preferably substantially homogeneous magnetic field. The carrier arranged in the magnetic field densifies the magnetic field lines in its environment, which results in magnetic field gradients which pull the ferromagnetic (or paramagnetic) attachment bodies against the carrier surface. The attachment bodies are consequently held in the reaction space in a static arrangement by the carrier. The suspension can freely flow past the attachment bodies without taking these along.

In another constructional form (dynamic arrangement) of the invention, the attachment bodies are held inside the reaction space, through which the suspension flows, in that there are provided magnetic field gradients which prevent the attachment bodies from leaving the reaction space. In this case, the attachment bodies may be freely movable in the reaction space. In order to prevent the attachment bodies from being attached to one another or to the vessel walls, which would result in a reduction of the effective attachment body surface, it is proposed that the attachment bodies should be kept in motion in the reaction space, particularly by means of stirring.

It is furthermore proposed that, after the suspension has been passed through the reaction space, preferably after washing liquid has subsequently been passed through the reaction space, the magnetic field gradients should be removed and that the attachment bodies should be collected in a collection space, preferably beneath the reaction space, for further processing, more especially for removing the deposited organic substances. All that needs to be done for collecting the attachment bodies is thus the de-energisation of the respective electromagnet, whereupon the attachment bodies drop into the collection space.

In order to obtain products which are as free from contamination as possible, it is proposed that washing liquid should be passed through the reaction space before the suspension or solution is passed therethrough.

The method according to the invention can also be successfully used for growing cell cultures, in that one passes a nutrient solution through the reaction space, in which magnetic, preferably ferromagnetic attachment bodies provided with a cell culture layer are held by magnetic field gradients in an open arrangement. The open arrangement ensures an undistributed cell growth; the attachment bodies are held inside the reaction space volume on account of the magnetic field gradients so that there is no risk of the attachment bodies being grasped by the nutrient solution flow and being flushed away. One can thus cultivate cells in a very high concentration and constantly cause fresh culture medium to flow past them, which ensures a high rate of cell growth.

The invention also relates to an apparatus for the performance of the method according to the invention, which is characterised by (a) a reaction vessel with an inlet and outlet for passing therethrough a separating liquid, more especially a suspension or solution containing cells, organelles or proteins, (b) a plurality of magnetic, preferably ferromagnetic attachment bodies inside the reaction vessel, which may be provided with an absorption layer, which is specifically active for one or several test substances, or with a cell culture layer, and (c) a magnet arrangement for producing magnet field gradients which keep the attachment bodies in a reaction volume inside the reaction vessel.

With constructionally simple means it is ensured that the attachment bodies are kept in the reaction volume, if necessary at a greater or lesser distance from one another, and are not taken along by the flow. Carrier structures, such as fine-mesh sieves or the like, for the mechanical fixing of the attachment bodies or for enclosing the attachment bodies in the reaction vessel, which increase the flow resistance correspondingly, can be dispensed with.

One obtains an advantageously large effective surface with a given volume proportion of the attachment bodies if the preferably substantially spherical attachment bodies have dimensions of between 10 and 200 $\mu$m, preferably between 25 and 100 $\mu$m.

In a first constructional form of the apparatus according to the invention, there is provided a filigree-like, ferromagnetic carrier body which fills the reaction volume and through which a magnetic field passes. On account of the filigree structure, there are locally produced magnetic field gradients which pull the attachment bodies towards the carrier body surface. The carrier body ensures an approximately uniform distribution of the attachment bodies over the reaction volume. Since the carrier body does not have to fix the attachment bodies mechanically, it may be correspondingly light in construction and present a slight flow resistance.

If, as provided for according to the invention, the substantially homogeneous magnetic field extends transversely to the flow direction, the attachment bodies mainly attach themselves to surfaces of the carrier body which are parallel to the flow direction (and perpendicular to the magnetic field direction) and therefore the separating liquid advantageously flows around them virtually on every side.

In order to hold the ferromagnetic attachment bodies on the ferromagnetic carrier body, there suffices a relatively weak magnetic field of between 0.05 and 0.5 Tesla, preferably 0.01 and 0.1 Tesla, and ideally of approximately 0.03 Tesla.

The production costs are low if the carrier body consists of wire, preferably high-quality steel wire, with a wire diameter that is in the range of the dimension of the attachment bodies. With such a wire diameter, the magnetic forces acting on the attachment body are highest.

The wire body may be grid or sieve-like in construction or may be formed from arbitrarily bent wire (similar to steel wool).

A sufficient concentration of the attachment bodies with an advantageously low flow resistance is ensured if the mean distance between adjacent wire pieces is 5 to 200 times, preferably 10 to 100 times the wire diameter.

One obtains the desired homogeneous magnetic field extending transversely to the flow direction in a simple manner in that the reaction vessel is placed between the pole shoes of a magnet.

Instead of the magnetic fixation of the attachment bodies to the carrier body, provision may be made for there being produced by the magnet arrangement, at least at the outflow end of the reaction volume at which the separating liquid leaves the reaction volume, a magnetic field gradient which, in the case of ferromagnetic attachment bodies, drops towards the outside. This magnetic field gradient exerts a repelling force on the attachment bodies which are taken along by the flow of the separating liquid and thus retains these bodies in the reaction volume. The mentioned carrier body can be dispensed with, so that the attachment bodies are freely movable in the reaction volume and the entire surface thereof is available for their specific attachment.

In order to prevent the attachment bodies from agglomerating in the reaction volume or settling on the vessel walls, there is proposed a stirring device for the attachment bodies in the reaction volume. This device is preferably formed by a rotating stirring bar which may be concentric with the reaction vessel axis and which moves the attachment bodies in the opposite direction to the flow direction of the separating liquid. This ensures that the attachment bodies are substantially uniformly distributed over the entire reaction volume during operation.

In order to allow the attachment bodies to be fed into the reaction space with simple means, it is proposed that the reaction vessel should be provided with an introduction opening for a hollow needle or a hose for feeding the attachment bodies. The introduction opening may additionally serve as a vent.

The invention will hereinafter be explained with the aid of two exemplified embodiments and with reference to the drawings, in which:

FIG. 3 shows a lateral view of a second constructional form of the separating apparatus according to the invention.

Figure 1:
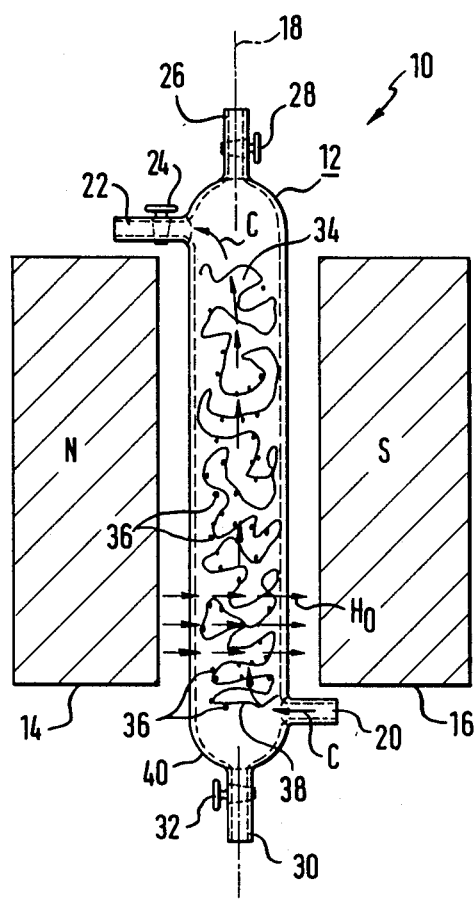
FIG. 1 shows a lateral view of a separating apparatus for organic substances according to the invention.

The separating apparatus 10 shown in FIG. 1 consists of a reaction vessel 12 which has been inserted between the pole shoes 14 and 16 of an electromagnet which is not shown in detail. The pole shoe 14, which is to the left in FIG. 1, is, for example, the north pole, and the pole shoe 16 is accordingly the south pole. A substantially homogeneous magnetic field $H_0$ prevails between the two pole shoes.

The reaction vessel 12 is substantially cylindrical and has a vertical cylinder axis 19 which is perpendicular to the magnetic field direction $H_0$. From its lower end there projects, to the right in FIG. 1, a hose connection socket 20, to which a suspension containing cells or organelles is fed through a feed line not shown. The suspension is discharged via another hose connection socket 22 which projects to the left at the upper end of the reaction vessel 12. A shut-of valve 24 has been ground into the reaction vessel 12, consisting of glass, in the upper hose connection socket 22.

From the upper end of the reaction vessel 12 there projects an introduction socket 26, through which it is possible to introduce into the reaction vessel interior attachment bodies called hereinafter 'pearls'. The introduction socket 26 can be shut off by means of a valve 28. Accordingly, there has been integrally formed with the lower end of the reaction vessel 12 a discharge socket 30 which can also be shut off by a valve 32. In a part of the reaction vessel interior designated the reaction volume 34, in the zone between the pole shoes 14 and 16, there has been inserted an arbitrarily bent, extremely fine steel wire 38 which serves as the carrier for the pearls 36; there may be introduced several of such steel wires into the reaction vessel interior. The steel wire has a diameter d (see FIG. 2) of 25 to 100 μm; the steel wire 38 has been agglomerated so loosely in the manner of steel wool that adjacent steel pieces are at an average distance from one another that corresponds to 10 to 100 times the diameter d. The intensity of the magnetic field $H_0$ is approximately 0.03 Tesla (300 Gauss).

The pearls 36 consist of beads in an adsorption material such as polyagarose or polyacrylamide and contain inclusions in a ferromagnetic material. Seveal types of these pearls are obtainable in the trade. For the specific bonding of specific cells, organelles or protein molecules, there is applied to the surface of the pearls 36 a substrate which is covalently bound to the pearl surface; however, there may be used a short-chain spacer which is also covalently bound. The diameter e of the pearls 36 (FIG. 2) is approximately 100 μm.

Figure 2:
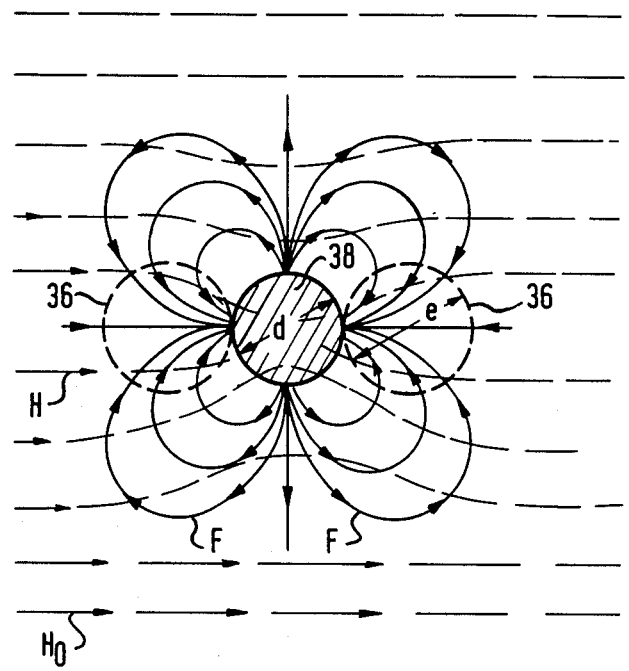
FIG. 2 shows the force field around a ferromagnetic wire in a homogeneous magnetic field.

On account of the magnetic field $H_0$, the pearls 36 are magnetically attracted by the windings of the steel wire 38 and are retained on the wire surface so that the pearls 36 stay in the reaction volume 34 in spite of the flow of the suspension through the reaction vessel 12 in the direction of the arrows C. In FIG. 2, the lines of force F acting on a ferromagnetic body are shown in solid lines. These lines come about on account of the concentration of the magnetic field lines H, indicated in broken lines, in the zone of the ferromagnetic wire 38. As has been stated, for example, in the magazine IEEE Transactions on Magnetics, VOL.MAG.-9, No. 3, September 1973, pages 303–306, this force, which is dependent on the magnetic field $H_0$ as well as on the local magnetic field gradient, is strongest if the diameter d of the wire 38 corresponds approximately to the diameter e of the attracted particle, which is the ferromagnetic pearl 36 herein. As emerges from FIG. 2, with the geometrical arrangement shown, the pearls 36 attach themselves in the direction of the field $H_0$ on one side or the other (to the right or left in FIG. 2) of the wire 38, whereas the pearls 36 are repelled in the plane which is perpendicular to the field direction $H_0$.

In FIG. 1, there are shown not to scale some windings of the wire 38 as well as some pearls 36 which are magnetically retained on the wire. In actual fact, the total volume of the pearls 36 is approximately 20% of the volume of the reaction space 34 between the pole shoes 14 and 16.

The method according to the invention for the separation of specific biological cells or organelles (possibly also proteins) from an organic suspension is as follows.

First, with the electromagnet energised, the pearls are introduced with the reaction volume 34 via the introduction socket 26, for example by means of a cannula, the reaction volume being simultaneously filled with a buffer solution. On account of the magnetic field $H_0$ and the resulting magnetic field gradients in the surface zone of the wire 38, the pearls 36 are pulled to the wire surface and are retained there. As the next step, washing liquid is passed via the sockets 20 and 22 through the reaction vessel 12 so as to remove any dirt or other undesirable substances from the reaction vessel 12. Now the suspension containing the cells or organelles to be separated is passed through the reaction vessel 12, possibly several times in circuit. The flow resistance of the filling of the reaction vessel 12, consisting of wire 38 and pearls 36, is comparatively low so that a relatively high flow velocity of the suspension is reached without difficulty. The total sojourn time of the suspension inside the reaction vessel 12 is up to four times the reaction half-life period of the specific bonding reaction of the cells or organelles to be separated.

Subsequently, washing liquid is passed through the reaction vessel 12, so as to wash organic substances which are not specifically bound to the pearls 36 away.

Finally, the electromagnet is de-energised so that the magnetic field $H_0$ as well as the corresponding magnetic field gradients in the zone of the wire 38 disappear. The pearls 36 thereupon drop and are collected at the lower approximately funnel-shaped end 40 of the reaction vessel 12. Now it is possible, by opening the valve 32, to remove the pearls 36 from the vessel 12 and to treat them in a further process step in such a way that the specifically bound cells and organelles (or proteins) are detached from the pearls 36.

Figure 4:
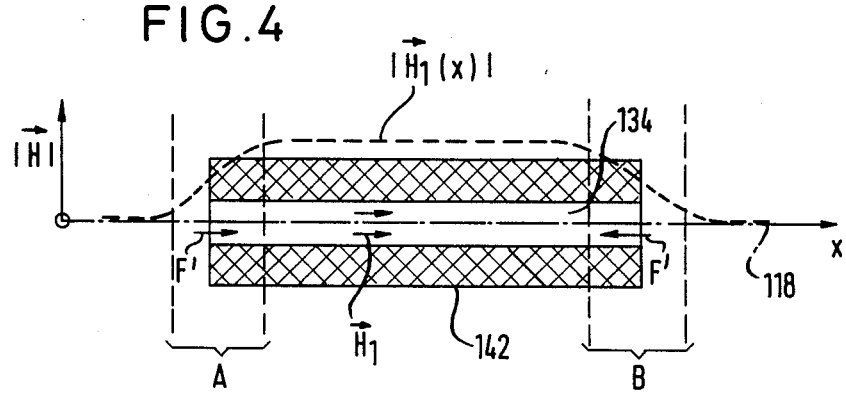
FIG. 4 shows a schematic diagram of the magnetic field pattern in the coil of the apparatus shown in FIG. 3.

In FIGS. 3 and 4, there is shown another constructional form of the separating apparatus according to the invention which is designated 110. This apparatus differs from the separating apparatus shown in FIGS. 1 and 2 substantially in that the ferromagnetic pearls 136 in the central zone of the reaction vessel 112 are freely movable and are prevented by magnetic field gradients from leaving the reaction volume 134 which is again substantially formed by the part of the reaction vessel interior which lies inside the electromagnet. The magnet is now formed by a cylindrical coil 142.

The reaction vessel 112 is again provided with a lower hose connection socket 120 and an upper hose connection socket 122, through which the organic suspension is fed and discharged. At the lower vessel end, there is provided in the same way a discharge socket 130 which can be shut off by means of a valve 132. At the lower vessel end, there is furthermore formed an introduction socket 126 for feeding the pearls 136. However, this introduction socket may be dispensed with if a vent 144 provided at the upper reaction vessel end is additionally used as an introduction opening for a pearl feeding needle or a pearl feeding hose.

At the upper reaction vessel end, there is mounted, so as to be rotatable by means of a pivot bearing 148 shown in a simplified manner, a stirring bar 146 which passes through the vessel interior. The stirring bar 146 is centrically arranged to the cylinder axis 118 of the substantially cylindrical reaction vessel 112. In the zone of the reaction volume 134, it carries blades 150 which have been twisted similar to a propeller and have an approximately circular contour and which, during a corresponding rotation of the bar 146, ensure that the pearls 136 impinging on the blades 150 are pushed downwardly and consequently opposite to the flow direction (arrows C) of the suspension. The reaction vessel 112 consisting of glass is in two parts so as to allow the stirring bar 146 to be inserted. Accordingly, the reaction vessel 12 shown in FIG. 1 may be designed in two parts.

The magnetic field gradients at the upper and lower ends of the coil 142 ensure that the ferromagnetic pearls 136 do not leave the reaction volume 134, that is to say the space inside the coil. This will be explained with reference to FIG. 4. In addition to the cross section of the cylindrical coil 142, which has been rotated through 90°, there has been plotted in a broken line the magnitude of the magnetic field $H_1$ at the locus of the cylinder axis 118; the space co-ordinate x plotted to the right applies both to the coil 142 and to the representation of the magnitude of the magnetic field $H_1$; the magnitude of the magnetic field $H_1$ has been plotted to the top.

One discerns that the magnetic field $H_1$ assumes a constant value in the central zone of the coil interior, drops in the zone of the two ends and finally becomes zero at a larger distance from the coil 142. The transition zones at the two ends with a continuously changing magnetic field magnitude are designated A and B. In the zones A and B there therefore prevails a magnetic field gradient which exerts on ferromagnetic (or paramagnetic) particles a force in the direction of the larger magnetic field, in other words to the coil interior. The corresponding force arrows designated F' are indicated in FIG. 4. Since the magnetic field is approximately constant in the radial direction in the hole zone of the coil, there also act on ferromagnetic particles located outside the axis 118 in the zones A and B magnetic forces which are directed into the coil interior. Ferromagnetic particles arranged in the coil interior are thus prevented from escaping by the gradients at the two coil ends. By contrast, inside the central coil zone between the end sections A and B, as shown in FIG. 4, the ferromagnetic particles are freely movable since, on account of the magnetic field being constant here, there do not prevail any magnetic field gradients. Instead of the described focussing magnetic field, there may be used, in other magnet forms, in principle a magnetic field with a singlefield gradient.

The separating apparatus 110 is used substantially in the same way for separating organic substances from suspensions as the separating apparatus 10 shown in FIGS. 1 and 2. Following the feeding of the ferromagnetic pearls 136, for example through the opening 144 by means of an appropriate hollow needle, and with the magnetic coil 142 energised and the vessel 112 filled with liquid, the pearls 136 are prevented by the magnetic field gradients at the lower and upper coil ends from dropping, on account of gravity, into the lower vessel end 140 outside the coil 142, on the one hand, and from being taken along by the flow of the suspension (in the direction of the arrows C) and finally leaving the vessel 112 through the hose connection piece 122, on the other hand. After washing liquid has been passed through the vessel 112, the suspension is passed through the vessel 112. The rotating stirring bar 146 (rotational speed: for example 30 revolutions/min) ensures, on the one hand, that the pearls 136 are neither lumped together nor settle on the vessel internal wall and, on the other hand, that at a higher flow velocity of the supsension the tendency of the pearls 136 to accumulate at the upper coil end is counteracted.

When the specific cells, organelles or proteins have become attached to the pearls, the feeding of the suspension is interrupted and then washing liquid may be passed through the vessel 112. Subsequently, the magnet 142 is de-energised so that the pearls 136 drop into the lower end 140 of the vessel 112 and can be discharged through the valve 132 for further treatment.

The afore-described separating apparatuses 10 and 110 generally serve for keeping pearls serving as attachment bodies in a reaction volume through which the flow passes at a distance from one another, in other words in an open arrangement. Inside the reaction volume, the pearls may be kept substantially stationary in a static arrangement (FIGS. 1 and 2) or may be freely movable inside the volume in a dynamic arrangement (FIGS. 3 and 4). As described above, the medium to be passed through the reaction volume may be a suspension consisting of cells, organelles or proteins; the pearls serve as adsorption pearls, to which the cells or organelles to be separated from the suspension become attached.

The static or dynamic open arrangement of pearls may however also be successfully used for the cultivation of cell cultures. For this purpose, the attachment bodies are "inocculated" with cell cultures in a first step, whereupon a greater or lesser cell culture layer is formed on the pearls. This inocculation may be effected inside the reaction space volume, that is to say inside the apparatus 10 or 110; for the cell culture cultivation proper, a nutrient solution is subsequently passed through the reaction space volume, the cell culture pearls being kept by the magnetic field gradients in the open static or dynamic arrangement. Magnetic field gradients thus ensure that the ferromagnetic pearls are not taken along by the nutrient solution flow. Since the pearls fill only a relatively small proportion of the reaction space volume, large quantities of cell cultures can be grown. Since nutrient solution is constantly passed along the cells, a high cell culture production rate comes about.

I claim:

1. An apparatus for the separation of cells, organelles, or proteins from a suspension or solution thereof, comprising:
   (a) a reaction vessel with an inlet and outlet for passing the suspension or solution therethrough;
   (b) a plurality of magnetic attachment bodies inside the reaction vessel which bodies are provided with an adsorption layer which is specifically active on test substances or with a cell culture layer; and
   (c) a wire ferromagnetic carrier body within a reaction volume and through which a magnetic field passes; and
   (d) a magnet arrangement for producing magnetic field gradients which keeps the attachment bodies in the reaction volume inside the reaction vessel.

2. An apparatus as claimed in claim 1 wherein the attachment bodies are spherical and have a diameter of between 10 and 200 μm.

3. An apparatus as claimed in claim 1 wherein the magnetic field is substantially homogeneous and extends transversely to the flow direction of the suspension or solution passing through the reaction vessel.

4. An apparatus as claimed in claim 3 wherein the intensity of the magnetic field is between 0.005 and 0.5 Tesla.

5. An apparatus as claimed in claim 4 wherein the carrier body is formed from wire, the wire diameter being in the range of the diameter of the attachment bodies.

6. An apparatus as claimed in claim 5 wherein the construction of the carrier body is grid- or sieve-like.

7. An apparatus as claimed in claim 5 wherein the carrier body is formed from aribitrarily bent wire.

8. An apparatus as claimed in claim 7 wherein the mean distance between adjacent wire pieces is 5 to 200 times the wire diameter.

9. An apparatus as claimed in claim 8 wherein the reaction vessel is inserted between the pole shoes of a magnet.

10. An apparatus as claimed in claim 9 wherein a magnetic field gradient, is produced by a magnet arrangement at least at the outflow end of the reaction volume at which the suspension or solution leaves the reaction volume.

11. An apparatus as claimed in claim 10 wherein the reaction vessel is cylindrical and has been inserted into the hole of a cylindrical coil.

12. An apparatus as claimed in claim 10 having an introduction opening, which serves for ventilation, in the reaction vessel for a hollow needle or a hose for feeding attachment bodies into the reaction volume.

13. An apparatus as claimed in claim 12 having a collection space, which is provided with a discharge valve, for the attachment bodies beneath the reaction volume.

14. An apparatus for the separation of cells, organelles, or proteins from a suspension or solution thereof, comprising:
   (a) a reaction vessel with an inlet and outlet for passing the suspension or solution therethrough;
   (b) a plurality of magnetic attachment bodies inside the reaction vessel which bodies are provided with an adsorption layer which is specifically active on test substances or with a cell culture layer;
   (c) having a stirring bar which is arranged concentrically with the reaction vessel and which moves the attachment bodies in the direction opposite to the flow direction of the suspension or solution passing through the vessel; and
   (d) a magnet arrangement for producing magnetic field gradients which keeps the attachment bodies in a reaction volume inside the reaction vessel.

* * * * *